United States Patent [19]

Mondre

[11] Patent Number: 5,035,252

[45] Date of Patent: Jul. 30, 1991

[54] NICOTINE-CONTAINING DENTAL FLOSS

[76] Inventor: Steven J. Mondre, 370 E76 B1501, New York, N.Y. 10021

[21] Appl. No.: 627,657

[22] Filed: Dec. 14, 1990

[51] Int. Cl.$^5$ .................. A61C 15/00; A24F 47/00
[52] U.S. Cl. .................. 132/321; 132/329; 131/270
[58] Field of Search .............. 131/270; 132/321, 329; 514/813, 343; 424/412

[56] References Cited

U.S. PATENT DOCUMENTS

| | | | |
|---|---|---|---|
| 3,699,979 | 10/1972 | Muhler et al. | 132/321 |
| 4,098,879 | 7/1978 | Cousse et al. | 424/52 |
| 4,162,688 | 7/1979 | Tarrson et al. | 132/92 A |
| 4,276,890 | 7/1981 | Fichera | 131/270 |
| 4,548,219 | 10/1985 | Newman et al. | 132/321 |
| 4,597,961 | 7/1986 | Etscorn | 424/28 |
| 4,627,975 | 12/1986 | Lynch | 424/49 |
| 4,632,937 | 12/1986 | Lynch | 514/470 |
| 4,638,823 | 1/1987 | Newman | 132/321 |
| 4,736,755 | 4/1988 | Oldham et al. | 131/270 |
| 4,839,174 | 6/1989 | Baker | 424/447 |
| 4,867,181 | 9/1989 | Smolko | 131/270 |

FOREIGN PATENT DOCUMENTS 251642  1/1988  EPO

OTHER PUBLICATIONS

Research Disclosure 23915, Anonymous, "Smoking Substitute Composition", March, 1984.

*Primary Examiner*—John J. Wilson
*Assistant Examiner*—Cindy A. Cherichetti
*Attorney, Agent, or Firm*—Hedman, Gibson, Costigan & Hoare

[57] ABSTRACT

Nicotine treated dental floss is disclosed which is useful in alleviating tobacco smokers' urges to smoke.

19 Claims, No Drawings

NICOTINE-CONTAINING DENTAL FLOSS

FIELD OF THE INVENTION

The present invention relates to dental floss. More particularly, the present invention relates to dental floss treated with nicotine and preferably to nicotine-containing dental floss. Most particularly, the present invention relates to a novel dental floss combination, and related method, for alleviating the urge to smoke tobacco while at the same time providing for the beneficial effects resulting from frequent dental flossing.

BACKGROUND OF THE INVENTION

Many persons who have acquired the habit of smoking tobacco are desirous of quitting. However, the addicting effects of tobacco smoking make it difficult for smokers to quit. Further, tobacco smoke is known to have deleterious effects to a person's teeth, gums and periodontal areas such as discoloration and gingivitis.

The health hazards from tobacco smoking are well established. Of the approximately 4,000 by-products of combustion found in cigarette smoke, many of which are known carcinogens, the three substances studied most have been tars, carbon monoxide and nicotine. Tars and carbon monoxide have been directly implicated in the production or exacerbation of numerous health disorders.

Thus, tars are the causative agents in cigarette smoke most implicated in the induction of cancers such as lung, larynx, oral cavity, esophageal, bladder, kidney, pancreatic, stomach and uterine and cervix cancers. Tars are also considered responsible for the induction of the hepatic microsomal enzyme systems which result in more rapid deactivation of a variety of drugs such as benzodiazepines as well as anti-depressants and analgesics. Tars are also responsible for the production of bronco pulmonary diseases, including pulmonary emphysema, chronic bronchitis, and smokers respiratory syndrome.

Carbon monoxide, a deadly gas, is an important health hazard even in minute quantities because it combines with the hemoglobin in the blood so that the hemoglobin can no longer carry sufficient oxygen. Moreover, the stimulant effect of the nicotine in the smoke causes an increase in cardiac workload and oxygen demand, whereas the carbon monoxide effectly blocks the ability of the heart muscle to capture the needed oxygen. In other words, carbon monoxide and nicotine work together in a synergistically negative manner in a way which often results in muscular hypoxia or anoxia and ultimately in cardiac damage. In addition, carbon monoxide has also been implicated as a causative agent in the development of such disorders as coronary artery disease and atherosclerosis.

Nicotine appears to be the most pharmacologically active substance in tobacco smoke, yet it appears to be not as significant from a health standpoint as the tars and carbon monoxide. However, nicotine is very important from another standpoint, i.e. it is the reinforcing substance in tobacco smoke which initiates and maintains the addiction. In this respect, a theme commonly heard among workers in the field of smoking research is: "People would be disinclined to smoke cigarettes if an alternate route of nicotine delivery could be devised."

Several such attempts have been made to administer nicotine in alternate ways, but with varying and generally ineffective results. For example, nicotine-containing pills have been studied; however, effective blood levels of nicotine are not achieved because drugs absorbed in the stomach pass through the liver first where, in this case, 80–90 percent of nicotine deactivation occurs. Similar findings have been demonstrated with nicotine chewing gum although it has been sufficiently successful to warrant its marketing.

There are other long established and traditional ways of absorbing nicotine through the mouth, including chewing tobacco, snuff and products which constitute diffusion bags of tobacco, all of such means relying on oral (or nasal) absorption of nicotine through the mucous membrane. However, because of the taste and other sensory effects of tobacco, such a manner of satisfying the nicotine habit is acceptable to only a very limited number of persons. Moreover, these habits still require the utilization of tobacco, and such use remains a problem especially for people with gum, mouth or throat problems as a result of long-term tobacco chewing or snuff "dipping" and who are unable to quit.

With regard to the nicotine gum referred to above, it has produced mouth ulcers in a number of individuals resulting in its rejection. In addition, the nicotine gum produces some gastric absorption with the resultant first pass through the liver and consequent rapid loss of activity. Moreover, people with artificial teeth have difficulty with gum in general; this is important as many people who experience the medical problems associated with years of smoking also tend to have generally poor dental hygiene and/or dental quality, and may also have artificial teeth.

Nicotine itself has been subjected to considerable study. Nicotine is a liquid alkaloid which is colorless, volatile and strongly alkaline. On exposure to air it turns brown. It is known to be very lipid soluble. The Merck Index, 9th Edition, 1976, page 847, indicates that nicotine base is readily absorbed through mucous membrane and intact skin, but the salts are not. On the other hand, nicotine has no known therapeutic application (The Pharmacological Basis of Therapeutics, fifth edition, Goodman and Gilman, 1970, page 588) and has been primarily used in research as an experimental tool for investigating neural function.

It is known in the art to incorporate nicotine into lozenges and chewing gum so as to provide for a means of dispensing nicotine into a person's system so as to overcome the urge to smoke. However, such chewing gums and lozenges, such as described in published French Patent Application No. 2 608 156 can cause nausea in the person using such gums and/or lozenges due to the ingestion of nicotine into the stomach and other portions of the digestive tract.

It has been proposed that a nicotine-containing lozenge be compounded with lactose (or a lactose-containing substance) a known antidote to nicotine poisoning and the unpleasant nausea and discomforts associated with nicotine ingestion, such as described in published European Patent Application No. 0 251 642.

However, in all cases of nicotine-containing lozenges and/or chewing gums, it is believed that a large portion of the nicotine is not effectively absorbed into the blood stream, thereby reducing to a certain degree the beneficial effect of smoking urge suppression sought to be achieved. At the same time, the necessary carriers in lozenges and chewing gums, i.e. those comprised of sugars and like substances, have a tendency to promote dental decay in the nature of dental caries, particularly in the interproximal surfaces of the teeth.

In Etscorn, U.S. Pat. No. 4,597,961, there is described a method of transcutaneous application of nicotine through the use of an occlusive pad so that the nicotine is administered transdermally. The occlusive pad described therein is intended solely for external application.

None of the foregoing patents mention or suggest the application of nicotine to dental floss, nor the use of such nicotine-containing dental floss in the suppression of the urge to smoke.

Flossing of the teeth is known in the art to help remove plaque from the tooth surface. Further, it is known in the art to apply dentrifice medicaments to dental floss.

For example, Lynch, U.S. Pat. Nos. 4,632,937 and 4,627,975 discloses coating dental floss with a solution of a dentrifice formulation containing monoalkyl and dialkyl ethers of dianhydrohexitols, which is said to be effective in the treatment of oral surfaces and cavities to reduce irritation and plaque accumulation caused by the action of bacteria.

Similarly, Newman et al., U.S. Pat. No. 4,548,219, disclose a fluoride-coated dental floss which has bactericidal activity; and Tarrson et al., U.S. Pat. No. 4,162,688, disclose fluoride medicated dental floss and a dispenser for the wet application of fluoride to floss.

Cousse et al., U.S. Pat. No. 4,098,879, disclose impregnating dental floss with fluoride salts of certain pyridine compounds, alone or in combination with ethyl-3-nicotinate hydrofluoride or Vitamin B, as inhibiting dental plaque.

However, none of the prior art relating to dental floss describe treating the floss with nicotine and the advantages of employing dental floss in aiding individuals to quit smoking.

Surprisingly, applicant has found that by providing a nicotine-treated dental floss there is provided an article of manufacture which produces both a beneficial periodontal effect and aids in alleviating an individual's urge to engage in tobacco smoking.

SUMMARY OF THE INVENTION

It is, accordingly, an object of the present invention to overcome problems in the prior art, such as indicated above.

It is another object of the present invention to administer nicotine through the mouth using a delivery system comprised of nicotine-containing dental floss, especially for the purpose of satisfying a nicotine habit while minimizing or eliminating side effects caused by absorbing nicotine through the lungs along with products of combustion of tobacco, or through the digestive tract.

It is a further object of the present invention to provide a new method of assisting persons to break the habit of smoking tobacco or the use of any tobacco product, while at the same time providing for the beneficial effects of frequent dental flossing.

It is still another object of the present invention to provide a nicotine delivery system comprised of nicotine-containing dental floss.

These and other objects of the invention are broadly achieved by providing nicotine, a nicotine-containing compound to a monofilament dental floss, multifilament dental floss or the like, whereby the nicotine is applied to the oral cavity, preferably to the periodontal areas, and permitted to enter the body. Under such conditions the nicotine, being highly lipid soluble, is absorbed directly and rapidly through the oral tissues thereby satisfying the nicotine habit while minimizing or eliminating side effects which would otherwise be caused when absorbing nicotine through the lungs along with products of combustion, or through the digestive tract.

Such a delivery system as mentioned below can assist a person to quit smoking, and at the same time help to counter any possible deleterious dental effects, particularly deleterious periodontal effects, which often accompany longterm oral use of tobacco products.

A nicotine-containing dental floss may be used to supply the smoker with an alternate source of nicotine, for example, in the dose range of from 15 to 25 nanograms per liter of blood, so that the need for cigarettes is reduced or eliminated. Using such a mode of administration provides a number of beneficial results as follows:

1. An improved system becomes available to aid motivated smokers in eliminating their cigarette addiction. Numerous potent non-pharmacological factors which help maintain the cigarette addiction are the rituals involved with the act of smoking, including the sight of a pack of cigarettes, the smell, the taste, etc. These previously neutral cues acquire powerful reinforcing properties as a result of prolonged association with nicotine. Practice of the present system, however, assists in extinguishing these addiction-maintaining cues by supplying nicotine in the absence of such cues.

Indeed, a plurality of extinguishing techniques can be utilized in association with the present invention. Thus, instead of completely substituting the technique of the instant invention for smoking, an interspersing regimen can be adopted wherein the nicotine-containing dental floss according to the invention may be alternated with cigarettes to slowly extinguish the reinforcing properties of the non-pharmacological factors, and also reduce the severity of the initial termination of smoking as well as the incidence of relapse. As the non-pharmacological factors become reduced in importance, it then upon becomes easier to treat the nicotine addiction.

2. Patients with disorders such as emphysema, cardiac problems or lung cancer and who are unable to quit smoking thus exacerbating their medical problems, are able to satisfy their nicotine habit while sparing themselves further damage from the tars and carbon monoxides in tobacco smoke.

3. Nicotine absorbed through oral cavity, and particularly through the periodontal tissues, is not transported first through the liver where 80–90 percent of nicotine deactivation occurs, but goes directly and rapidly into systemic circulation with rapid rises in nicotine blood level. Thus, the nicotine habit can be satisfied while subjecting the body to far lesser quantities of nicotine.

Using the present system, blood levels of nicotine can be easily adjusted to acceptable and effective dosages for the suppression of craving by varying the amount and duration of nicotine delivery. This is difficult if not impossible to accomplish with nicotine gums, or nicotine lozenges, because the person's rate of chewing is a major factor which manipulates dosage.

5. People with gum, mouth and throat problems, as a result of long-term tobacco chewing or snuff "dipping" and who are unable to quit, are aided in giving up their habits with the use of the nicotine-containing dental floss, and, further, the regular use of floss is known to alleviate or lessen many gum and/or periodontal problems.

6. Other advantages compared to nicotine-containing gum include obviating the problems of mouth ulcers in some individuals; reduction of nicotine taste as a secondary reinforcer; provision of a less conspicuous form of nicotine consumption (a short period of dental flossing is much less conspicuous than gum chewing); usability by those who reject gum on the basis of taste and some denture wearers who cannot chew gum; and provision of an alternate mode of nicotine administration. In this latter respect, even if the use of nicotine-containing dental floss is only equal in effectiveness to nicotine gum for many persons, this will provide a further method of reducing smoking dependence, it being known in the field that different techniques work better for different individuals.

7. In the event that the subject of the instant invention becomes available over-the-counter (as are cigarettes, snuff, chewing tobacco, etc.), the instant invention will provide a means for those, unable or unwilling to quit smoking, to ingest nicotine without subjecting themselves and their environment to smoking with its attendant dangers of carbon monoxide and tars. As is now well-established, "second hand" smoke is recognized as a significant health hazard in our society, and may cost the economy hundreds of millions of dollars a year in lost productivity medical costs and related expenses.

Use of the present invention would also allow ingestion of nicotine in places where smoking is prohibited, to avoid the consequences of performance decrements resulting from acute withdrawals. Moreover, for women unable to quit smoking during pregnancy, the use of nicotine-containing dental floss would at least eliminate carbon monoxide, thereby avoiding the deleterious effects of smoking on the fetus due to the blocking effects of carbon monoxide on oxygen absorption.

DETAILED DESCRIPTION OF THE PRESENT INVENTION

To attain these objects, there is provided by the present invention dental floss which is treated with nicotine (or 3-(1-methyl-2-pyrrolidinyl) pyridine), a pharmacologically active derivative thereof, or a nicotine or nicotine derivative-containing compound, alone or in combination with a pharmaceutically acceptable carrier, which is useful in the alleviation of an individual's urge to smoke tobacco and in the prophylaxis of periodontal disease.

Many methods of treating the dental floss are contemplated by the present invention. It is only necessary that the treatment method provide a substantially uniform dispersal of nicotine, nicotine derivative or nicotine-containing compound on the surface of, or impregnated into, the dental floss. The dental floss can be of varying configuration, including mono-filament and multi-filament design, according to end use. In this manner, it is believed, although the inventor does not wish to be bound by any particular theory, that while flossing the nicotine dispersed on the surface, or into the body, of the dental floss, is released into the mouth of the individual and subsequently and rapidly absorbed through the gums and into the bloodstream, thereby providing quick relief from the urge to smoke.

Dosage and duration of nicotine administration according to the present invention can be controlled in several ways separately and/or in combination. In general, a carrier can be mixed with the nicotine which will either speed or slow its passage through the oral tissues and into the bloodstream. The thickness of the dental floss diameter of a monofilament dental floss, or the number of strands and/or size of strands of multifilament dental floss can be varied to either increase or decrease the amount of nicotine available to be transferred from the dental floss to the oral tissues. The concentration of nicotine in the dental floss can be either decreased or increased in order to reduce or increase the duration of effect of treatment or the amount of dosing.

In general, no additive is necessary to assist in the administration of nicotine, because nicotine base is very highly lipid soluble and is quickly and completely absorbed into the systemic circulation. However, should it be desirable to increase or decrease the rate of penetration, then the nicotine base can be carried by a suitable solvent such as propylene glycol, glycerin, mineral oil, polyethylene glycol, DMSO or alcohol. It may also be mixed with water in which the alkaloid is readily soluble, thereby forming a water soluble salt; such a salt, however, is less lipid soluble and penetrates the oral tissues more slowly than the alkaloid base.

It may be desirable to add a carrier which will slow absorption in view of the fact that nicotine is highly toxic. In this way, the nicotine may be diluted to reduce dangers of misuse; for example, the nicotine may be mixed with an oil such as indicated above. Other types of fillers may be utilized as well; for example, the nicotine may be retained in a gelatinous base.

Using nicotine-containing dental floss to effect nicotine delivery while varying the type of dental floss delivering the nicotine, varying the concentration of the nicotine, varying the carrier, if any for the nicotine, varying the quantity of nicotine, and/or varying manner in which the nicotine is retained, the dose and duration of nicotine administration are precisely controllable. Also, the total dosage and delivery rate can easily be adjusted to suit the needs of the particular patient, i.e. a different dose of nicotine will be desirable to reduce the craving of a one pack-a-day smoker versus a three pack-a-day smoker. According to the present invention, it is possible to mimic smoking in terms of the amount of nicotine delivered, thereby reducing or eliminating dependence on any form of tobacco.

In the practice of the present invention, the nicotine, nicotine derivative or nicotine-containing compound, such as nicotine oil, available commercially, may be used alone, or is dissolved in an orally acceptable carrier to form a nicotine-containing mixture. The mixture is stirred to substantially uniformly disperse the nicotine, nicotine derivative or nicotine-containing compound throughout the mixture. Preferred orally acceptable carriers are selected from the group comprising water, alcohols such as ethanol, propylene glycol, waxes such as polyethylene glycol (sold under the trademark "CARBOWAX" by Challenge Products of Osage Beach, Mo.), and glycerol, and sugar solutions.

It is further contemplated by the present invention to add a fluoride composition to the mixture. Suitable fluoride compositions are sodium fluoride, n-alkyl-3-pyridinium methanol fluoride as described in U.S. Pat. No. 4,098,879; and stannous fluoride as described in U.S. Pat. No. 4,548,219; both of which are incorporated herein by reference.

To the mixture may also be added dyes and flavorings such as cherry or orange flavor and oil of wintergreen. Other additives such as medicaments, astringents, detergents, polishing agents, sweeteners, gelling agents, thickeners, pigments and other antibacterial agents, such as those known to persons skilled in the art may be added to the nicotinemixture in amounts sufficient to impart their particular characteristic.

The string or floss, waxed or unwaxed, as commercially available, such as from John O. Butler Company of Chicago, Ill. is allowed to come into contact with the mixture, such as by soaking or drawing the string through the solution using an apparatus designed for that purpose. The mixture can be used as soaked or drawn, or is allowed to air dry and solidify in, or on the surface of, the floss. The preferred treated floss has a coating comprising from about 0.1 to about 0.8 mg of nicotine per inch of dental floss.

The article of manufacture of the present invention preferably comprises sufficient nicotine so that one flossing is substantially equivalent to the amount of nicotine released into the bloodstream by smoking a single cigarette. Preferably, one flossing comprises the release of from about 0.5 to about 2.0 mg nicotine, more preferably from about 0.7 to about 1.5 mg nicotine, and most preferably from about 1.0 to about 1.2 mg nicotine. Marlboro 100's, for example, are reported to contain 1.2 mg nicotine average per cigarette.

The individual desirous of quitting smoking need only floss in a normal manner with the nicotine-treated dental floss of the present invention to alleviate the urge to smoke. Preferably, the individual will floss once each in the morning and evening and at times where pangs to smoke occur during the day. In a preferred method of treatment, the individual will gradually reduce the number of daily flossings until the cravings disappear.

Additionally, the flossing has the beneficial effect of providing a prophylaxis of periodontal disease by aiding in the removal of plaque from the teeth. Thus, the present invention surprisingly succeeds in turning a bad habit, tobacco smoking, into a good habit of flossing, which is likely to continue even when the individual has no more smoking cravings.

The above-mentioned patents are hereby incorporated by reference.

Many variations of the present invention will suggest themselves to those skilled in the art in light of the above-detailed description. For example, any nicotine-containing compound may be employed. Further, the floss employed may be of any type, waxed or unwaxed. All such obvious modifications are within the full intended scope of the appended claims.

I claim:

1. An article of manufacture comprising dental floss having a substantially uniformly dispersed amount of nicotine, a nicotine derivative or nicotine-containing compound.

2. An article as defined in claim 1 wherein said nicotine, nicotine derivative or nicotine-containing compound is suspended in an orally acceptable carrier.

3. An article as defined in claim 2 wherein said carrier comprises water, alcohols, waxes and sugar solutions.

4. An article as defined in claim 3 wherein said carrier comprises water or polyethylene glycol wax.

5. An article as defined in claim 1 wherein said floss also has a substantially uniformly dispersed amount of fluorine or fluorine derivative.

6. An article as defined in claim 1 wherein said floss also has a substantially uniformly dispersed amount of a flavoring agent.

7. An article as defined in claim 1 wherein said nicotine, nicotine derivative or nicotine-containing compound is present in an amount of from about 0.1 to about 0.8 mg per inch of floss.

8. An article as defined in claim 1 wherein said dental floss is multi-stranded.

9. A process of manufacturing a nicotine-containing dental floss comprising:
   (a) dissolving nicotine, a nicotine derivative or nicotine-containing compound in an orally acceptable carrier to form a nicotine-containing mixture; and
   (b) applying the mixture obtained in (a) to dental floss.

10. A process as defined in claim 9 wherein said carrier is selected from the group consisting of water, alcohols, waxes and sugar solutions.

11. A process as defined in claim 10 wherein said carrier comprises water or polyethylene glycol wax.

12. A process as defined in claim 9 wherein, in step (a), there is further dissolved a flavoring agent.

13. A process as defined in claim 9 wherein, in step (a), there is further dissolved a fluorine compound or a fluorine derivative to said mixture.

14. A method of alleviating the urge to engage in tobacco smoking comprising flossing the teeth with an article of manufacture comprised of dental floss having a substantially uniformly dispersed amount of nicotine, a nicotine derivative or a nicotine-containing compound.

15. A method as defined in claim 14 wherein said nicotine, nicotine derivative or nicotine-containing compound is suspended in an orally acceptable carrier.

16. A method as defined in claim 15 wherein said carrier comprises water, alcohols, waxes or sugar solutions.

17. A method as defined in claim 16 wherein said carrier comprises water or polyethylene glycol wax.

18. A method as defined in claim 14 wherein said floss also has a substantially uniformly dispersed amount of a flavoring agent.

19. A method as defined in claim 14 wherein said floss also has a substantially uniformly dispersed amount of a fluorine or a fluorine derivative.

* * * * *